United States Patent [19]

Garrott, Jr.

[11] 4,040,963

[45] Aug. 9, 1977

[54] ANAEROBIC WASTE TREATMENT FACILITY

[76] Inventor: Warren A. Garrott, Jr., Box 4612, 1816 Douglass Drive, Jackson, Miss. 39216

[21] Appl. No.: 578,861

[22] Filed: May 19, 1975

[51] Int. Cl.² .............................................. C02C 1/14
[52] U.S. Cl. .................................. 210/219; 210/220; 210/242 A; 261/87
[58] Field of Search ................... 61/.5, 1 R; 126/270, 126/271; 195/1; 210/2, 11, 12, 16, 104, 170, 180, 173, 181, 187, 195 M, 220, 221 R, 219, 242 R, 525; 137/202; 261/87; 415/80, 88, 131; 259/8, 107, 108

[56] References Cited

U.S. PATENT DOCUMENTS

| 2,211,958 | 8/1940 | Mahaffey | 61/1 R X |
|---|---|---|---|
| 2,243,262 | 5/1941 | Smith | 137/202 |
| 2,248,893 | 7/1941 | Parent | 210/187 |
| 2,572,767 | 10/1951 | Schlenz | 210/12 X |
| 2,597,931 | 5/1952 | Hance | 261/87 X |
| 3,383,309 | 5/1968 | Chandler | 210/11 |
| 3,411,163 | 11/1968 | Myers, Jr. | 126/271 X |
| 3,537,267 | 11/1970 | Webb | 61/1 R X |
| 3,563,382 | 2/1971 | Regent | 210/104 |
| 3,568,836 | 3/1971 | Ray | 210/242 R X |
| 3,620,206 | 11/1971 | Harris, Jr. et al. | 126/271 |
| 3,627,135 | 12/1971 | Goodman | 210/195 M |
| 3,638,869 | 2/1972 | Zimmerman | 210/173 X |
| 3,838,199 | 9/1974 | Coe et al. | 210/2 X |
| 3,933,628 | 1/1976 | Varani | 210/12 |

FOREIGN PATENT DOCUMENTS

| 808,796 | 7/1951 | Germany | 415/131 |

Primary Examiner—Thomas G. Wyse
Assistant Examiner—Robert H. Spitzer
Attorney, Agent, or Firm—Cushman, Darby & Cushman

[57] ABSTRACT

An anaerobic waste treatment facility for producing methane gas or the like during anaerobic digestion of organic material. A digestor has a flexible cover therefor and apparatus associated therewith for removing evolved gases collected under the flexible cover at controlled rates. The flexible cover may assume an inflated, partially deflated, or completely deflated position. The digestor has an inlet, mixing zone, quiescent zone, clear zone, and an outlet. Liquid from the clear zone may be withdrawn and returned to pop-up rotary mixing apparatus in the mixing zone. A loading system for the digestor may comprise — in addition to a raw sewage inlet — a loading structure for receiving municipal garbage and the like. Apparatus is provided in the loading structure for substantially preventing the passage of non-digestible materials into the digestor, while allowing the passage of digestible materials entrained with liquid in the loading structure into the digestor.

4 Claims, 12 Drawing Figures

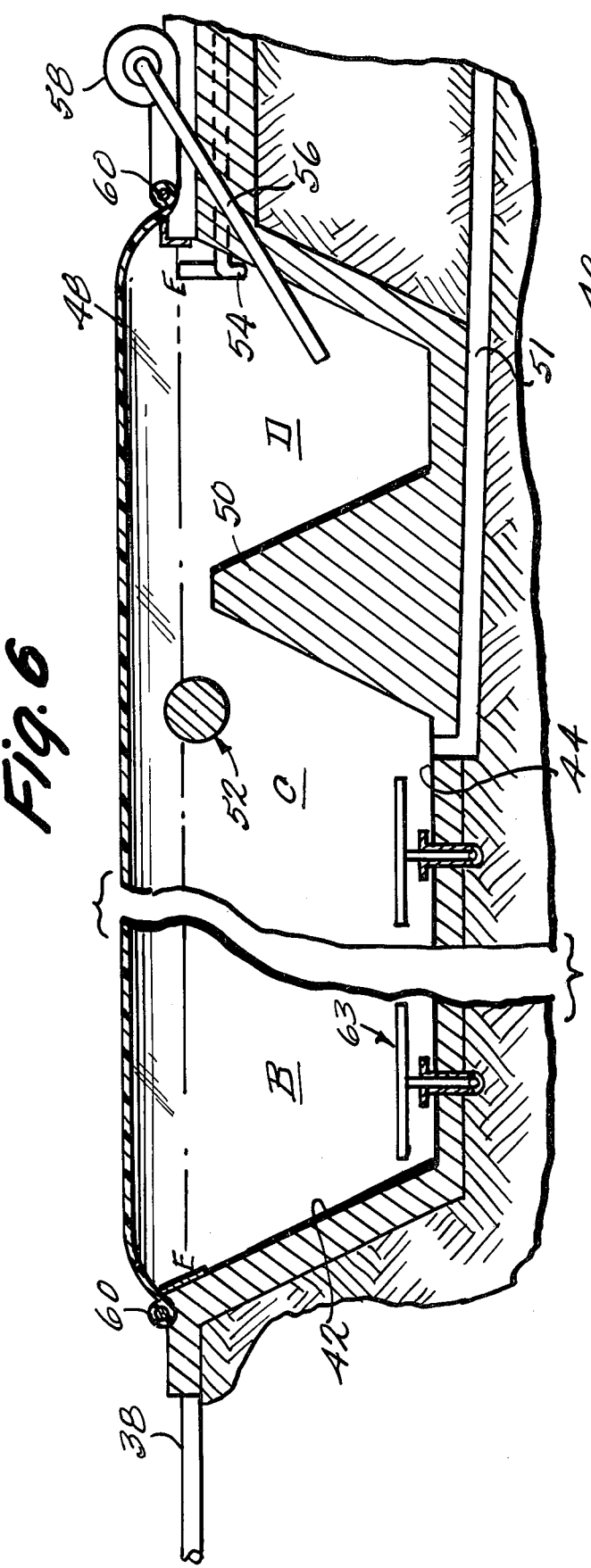
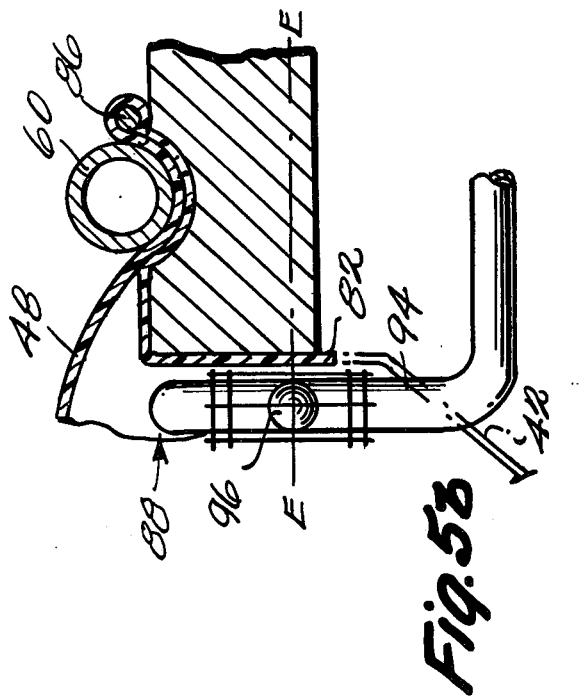
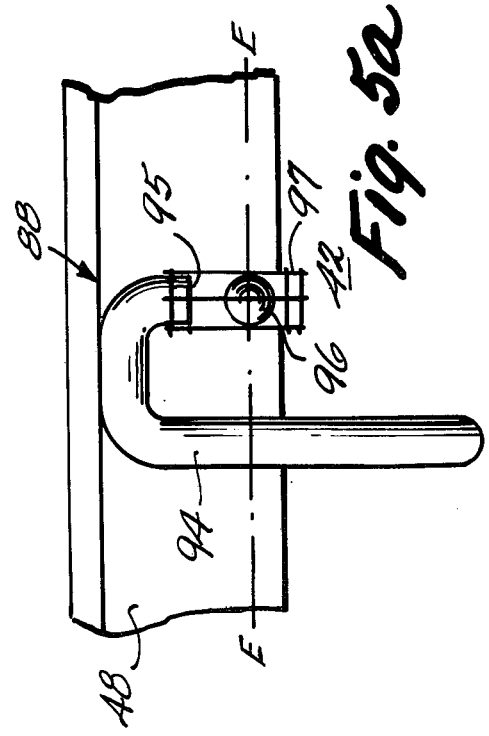

ANAEROBIC WASTE TREATMENT FACILITY

BACKGROUND AND SUMMARY OF THE INVENTION

The invention relates to waste treatment facilities in general and to means for separating organic wastes from other wastes, means for treating sewage and other liquid with organic wastes therein, and means for collecting methane and other energy producing gases evolved from anaerobic digestion of organic wastes and for maintaining good temperature conditions for anaerobic digestion in particular. Disposal of municipal garbage and the like, and treatment of sewage are major problems confronting society today, resulting in the expenditure of much energy, materials, and effort. According to the present invention, these wastes are disposed of or treated for ultimate disposal with a net generation of energy rather than a consumption thereof. This is accomplished by separation of organic components of municipal garbage, sewage and the like from the non-organic components thereof, and decomposition of the organic portion of the waste in the absence of oxygen (anaerobic digestion) to produce methane. Theoretically, each pound of organic waste digested can be converted to 6 cubic feet of methane, having a BTU content of approximately 6,000.

According to the present invention, production of methane is achieved with a minimum input of energy from exhaustible sources, such as fossil fuels or the like, and with materials that do not offer a significant potential for explosion of the methane gas produced. Radiant solar heat and insulative properties of gas are taken advantage of to produce methane under favorable conditions (approximately 40°–50° C) without the introduction of accessory heat from exhaustible sources, achievable results ensuing that promise improvement over conventional methane generation system proposals (such as shown in U.S. Pat. Nos. 1,757,262, 1,880,772, and 2,262,576).

According to the present invention, municipal garbage, raw sewage and the like are fed into a loading system, wherein the generally non-decomposable materials are separated from the decomposable organic materials. The non-decomposable materials may be otherwise separated and recycled. Then the organic material-containing liquid is fed into a digestor, and anaerobic decomposition of the organic material takes place. The digestor includes a mixing zone, quiescent zone, and clear zone, and mixing may be provided by suitable "pop-up" rotary mixing means, supplied with clear liquid from the clear zone. Treated liquid substantially free or organic material may be removed from the upper portion of the clear zone, and removed from the digestor. Methane gas and the like evolved by the digestor is collected by a digester cover of flexible material. Acculated gas between the flexible cover and the liquid in the digestor is removed by suitable means for ultimate utilization. The flexible cover may assume an inflated position, wherein heat in the digestor is conserved, a partially deflated position wherein radiant heat absorbed by the cover is transferred to the liquid being treated, and a completely deflated position wherein the liquid is allowed to cool. In this way ideal temperature conditions for anaerobic digestion may be maintained with a minimum energy input, and potential of sparking by frictional movement between components is substantially eliminated.

It is the primary object of the present invention to provide an improved waste treatment facility. This and other objects of the invention will become clear from an inspection of the detailed description of the invention, and from the appended claims.

BRIEF DESCRIPTION OF THE DRAWINGS

FIGS. 5a and 5b are front and side views respectively of exemplary evolved gas removal means that may be used in the digestor of FIG. 4;

FIG. 6 is a cross-sectional diagrammatic view of the digestor shown in FIG. 4;

DETAILED DESCRIPTION OF THE DRAWINGS

Figure 1:
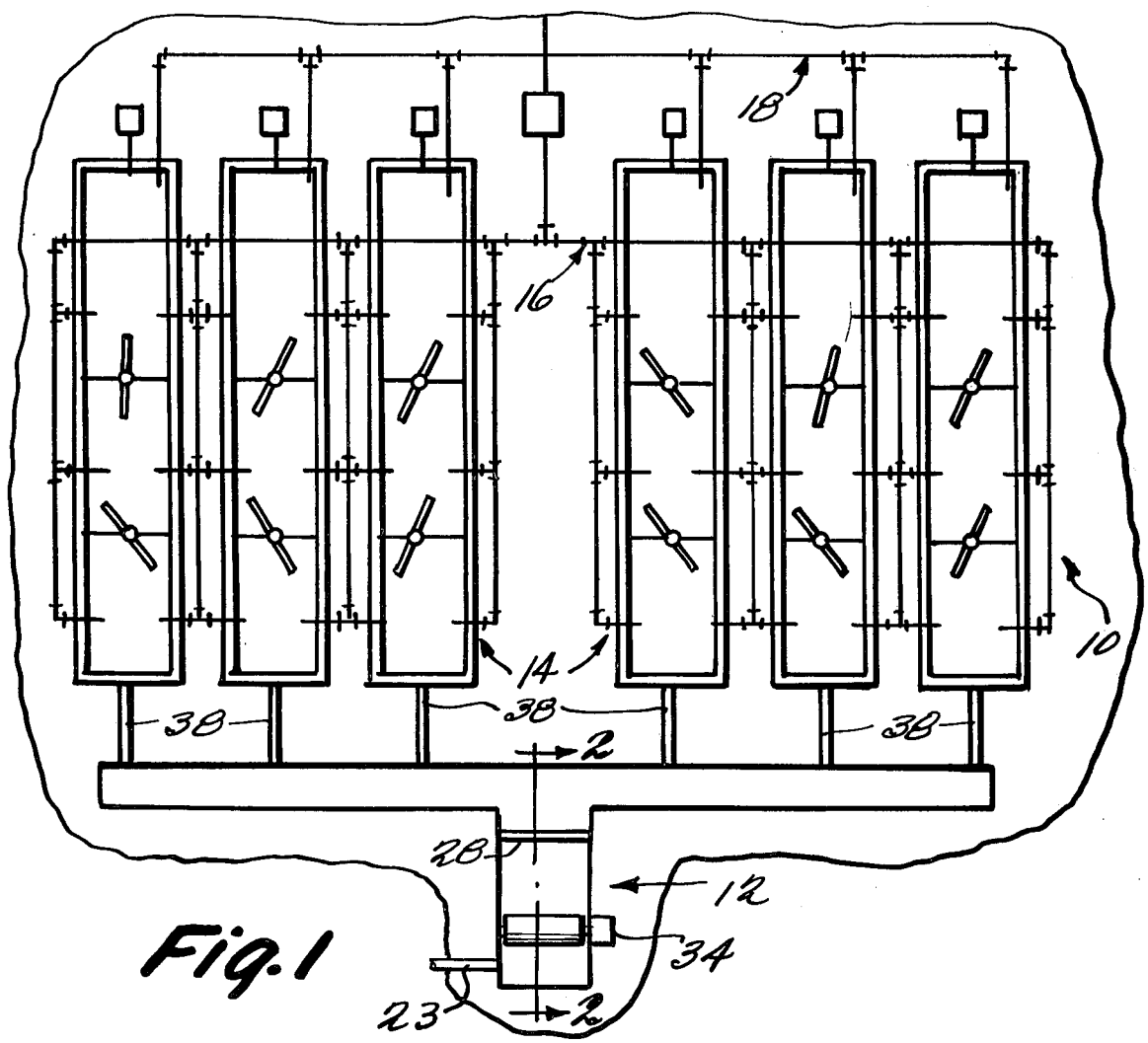
FIG. 1 is a top plan diagrammatic view of an exemplary anaerobic waste treatment facility according to the present invention.

An anaerobic waste treatment facility according to the present invention is shown generally at 10 in FIG. 1. The facility 10 generally consists of several major components, a loading system 12, one or more digestors 14, an evolved gas removal system 16, and a digester effluent system 18. The waste treatment facility 10 according to the present invention anaerobically treats sewage and/or municipal garbage to purify the sewage and to generate and collect methane and other useable gaseous products of the anaerobic digestion of the organic materials within the digestor 14.

Loading System

Figure 2:
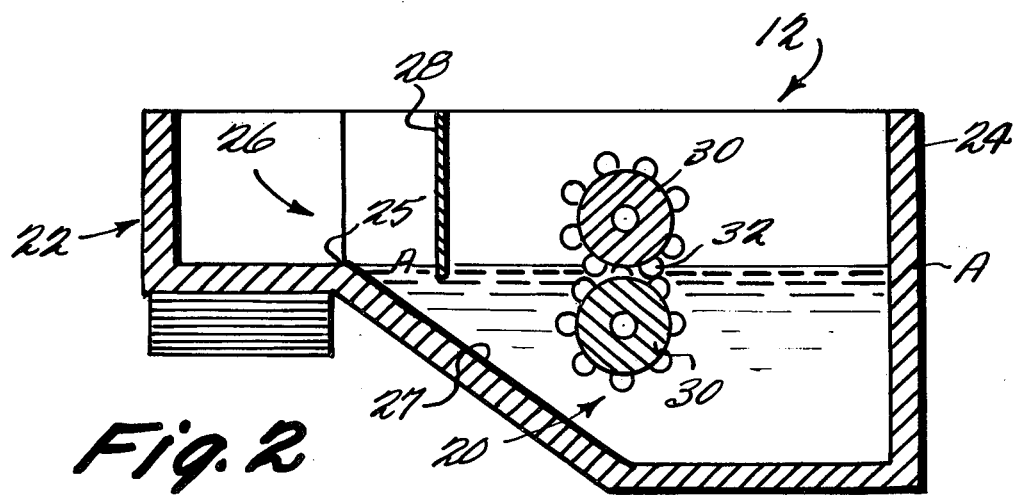
FIG. 2 is a sectional view taken along lines 2—2 of FIG. 1 showing an exemplary loading structure according to the present invention.

The loading system 12 is especially useful for facilities 10 which are to receive municipal garbage as well as sewage. When only sewage is to be received by the facility 10, the loading system 12 may be eliminated if desired, and replaced by only a sewage inflow pipe or system. The loading system 12 preferably comprises a loading structure 20 (see FIG. 2 especially) and a loading flume 22 in liquid communication with the structure 20. The loading structure 20 preferably comprises a trough 24 having an open top, and an open side 26 thereof; the open side 26 allows liquid communication between the trough 24 and the flume 22 by allowing liquid flowing over top portion 25 of side 26 to flow into flume 22. Sloped side wall portion 27 of side 26 provides for sinkable items to be returned to the bottom of the trough 24. Raw sewage from a pipe 23 or the like flows into the trough 24, and municipal garbage or the like may be dumped into the trough 24 through the open top thereof. Sewage in the trough 24 generally assumes a level A—A.

In order to substantially prevent the non-organic portions of municipal garbage being dumped into the trough 24 from passing into the digestor(s) 14, a baffle 28 and crushing rollers 30 or the like may be provided. The baffle 28 may extend from a point above the liquid level A—A in the trough 24 to a point at or just below or just above the normal liquid level A—A, and prevents the passage of any materials that float on the surface of the liquid from the trough 24 into the flume 22, such as plastics, rubber, etc. These materials will normally float on top of floatable saturated organic materials too, and the baffle 28 may be arranged so that saturated organic materials may pass thereunder, while plastics, rubber, and the like may not. The accumulated plastics, rubber, and the like may be removed from behind the baffle 28 by any suitable means.

Crushing rollers 30 or the like may be provided for crushing bottles or cans or the like that have air entrained therein and therefore float on the surface of the liquid in the trough 24. The rollers 30 rotate generally about horizontal axis, and have an area of interengagement therebetween that is disposed at generally the level of the liquid in the trough 24. Power means 34 rotate the rollers 30 to engage floating containers, crush them, and move them to the other side thereof. The crushed containers then fall to the bottom of the trough 24 along with other cans and heavy objects that orginally fell to the bottom of the trough 24 when dumped into the trough. Heavy materials on the bottom of the trough may be removed and/or separated by suitable conventional means. For instance, the sinkable items may be removed by conveyor or liftable container, the iron items may be separated magnetically, the glass may be crushed and removed by sifting, and the remainder may be separated by air blast or other suitable means.

Figure 3:
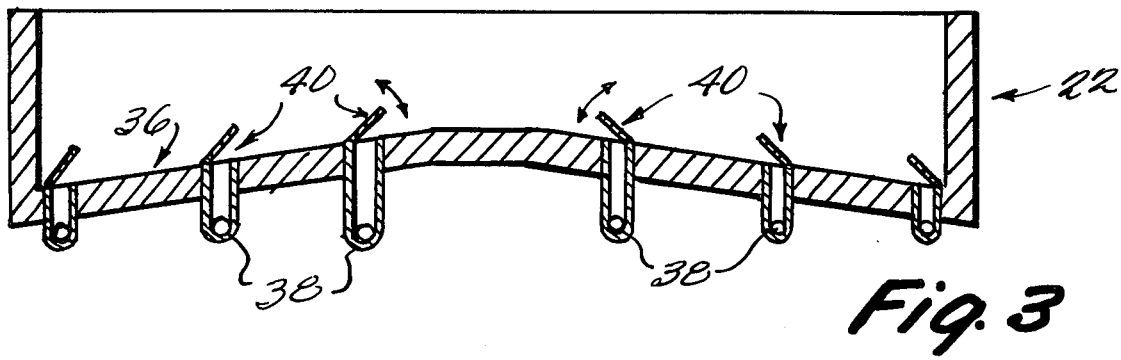
FIG. 3 is a sectional view taken generally along lines 3—3 of FIG. 1 showing an exemplary loading flume according to the present invention.

The loading flume 22 (see FIG. 3) may comprise a structure for feeding the sewage and organic matter in municipal garbage entrained therewith to one or more digestors 14. The flume 22 may have a bottom 36 thereof that is relatively high at the middle portion thereof in communication with the trough 24, and then slopes downwardly on either side. One or more inlets 38 for digestors 14 may be disposed in the floor 36 of the flume 22, and each inlet 38 may have a trap door 40 or the like covering it for selectively admitting liquid with entrained organic material from the flume into the digestor 14 corresponding to an inlet 38. The door 40 of the digestor 14 may be controlled so as to maintain appropriate liquid levels in the digestors 14.

It will thus be seen that municipal garbage, agricultural wastes, or the like and raw sewage enter the loading trough 24, wherein the organic material in the municipal garbage or the like is saturated, and the saturated organic material is allowed to flow with the liquid into the flume 22. Light non-digestible materials such as plastic, rubber, etc., are removed by the baffle(s) 28, items with entrained air are crushed by rollers 30, and sinkable components of the municipal garbage or the like settle to the bottom of the trough 24 and are removed by suitable means. The liquid with organic material therein then is selectively passed from the loading flume 22 to various digestors 14.

Anaerobic Digestor

Each anaerobic digestor 14 (see FIGS. 4 and 6 especially) comprises a plurality of side walls 42 (the number depending upon the shape of the digestor), a bottom 44, and an open top defined by a peripheral top surface 46. The open top is preferably covered to prevent entrance of oxygen into the digestor 14 by a cover 48 made of flexible material and having a surface area generally larger than the surface area of the open top of the digestor. The cover 48 will be described in more detail later. The digestor 14 has various zones defined therein, a mixing zone B in the area of the digestor near the inlet 38, a quiescent zone C, and a clear zone D. The quiescent zone C and clear zone D are preferably separated by suitable means for preventing large particles from entering the clear zone D; such means may take the form of a weir 50 and a skimmer 52. The skimmer 52 may float on the level of liquid E—E in the digestor 14, and prevent the passage of floatable inert materials and the like into the clear zone D. Solids settling to the bottom 44 of digestor 14 adjacent the weir 50 may be removed through conduit 51 of other suitable means, and may be otherwise treated or disposed of in any conventional manner.

Liquid in the clear zone may be removed by overflow pipe 54 or the like and passed into effluent system 18. As shown in the drawings, the structure 54 includes a pipe having an open top thereof adapted to be disposed at the desired liquid level E—E in the digestor 14. The introduction of liquid through inlet 38, the withdrawal of clear liquid through pipe 54, and the recirculation of some liquid from clear zone D to mixing zone A in a manner to be further described, cause the contents of the digestor 14 to flow toward the overflow structure 54. Liquid removed by the pipe 54 or the like will be treated liquid, having most of the organic materials removed therefrom, and may be further treated by other conventional means (i.e. a chlorine plant), or otherwise disposed of through effluent system 18.

Liquid from the lower portions of zone D — which may still have significant amounts of organic material therein, may be periodically (or intermittently or continuously) removed from the zone D and recirculated back to the mixing zone B. The recirculating means may take the form — as shown most clearly in FIGS. 4, 6 and 7a — of first pipe means 56, a pump 58, recirculating second pipe means 60, third pipe means 62, and a mixing rotor(s) 63. The first pipe 56 extends from the lower interior of zone D to the exterior peripheral top surface 46 of the digestor 14, preferably extending through a wall 42 of the digestor 14 so as not to interfere with the cover 48. A pump 58 when operated forces liquid from zone D into recirculating pipes 60, which pipes are preferably disposed around the peripheral top surface 46 of the digestor 14. Preferably, the pipes 60 are not covered by anything so that the water circulating therethrough may be heated by solar radiation or the like. The exterior surfaces of the pipes 60 may be painted black (or otherwise suitably treated) so that radiant energy may be more readily absorbed thereby heating the liquid therein. It is desirable to keep the water within the digestor 14 relatively warm (i.e. as close to 65° C as practical without exceeding 65° C) so that the full action of the mesophilic and thermophilic bacteria in the digestor 14 is taken advantage of. If enough heating from solar radiation is not possible to maintain the temperature of the liquid in digestor 14 at least between 40° and 50° C (for good gas evolution), as where the ambient air is low in temperature, then an auxiliary heating means 59 in communication with recirculating pipes 60 may be provided; however, the use of the means 59 is to be avoided or minimized so that the net energy of products that may be produced by the facility is maximized.

Pipe means 62 or the like in communication with recirculating pipes 60 return the liquid under pressure in pipes 60 to the mixing zone B. The pipes 62 may enter the digestor from the bottom 44 or a side wall 42 thereof in order to avoid interference with the flexible cover 48, and so that they may be thermally insulated by the ground or the like when extending from the pipes 60 to the mixing means 63.

The mixing means 63 preferably comprises a first conduit 64 that is stationary with respect to the digestor 14 and in fluid communication with the third pipe means 62, and a conduit member 66 that is vertically rotatably movable with respect to the member 64. The stationary conduit 64 may have an interior sleeve 67 thereof for guiding the vertical and rotative movement of the member 66 with respect thereto. Collars or rings 68 and 69 on sleeve 67 are adapted to cooperate with rings 70 and 71 formed on the exterior of conduit 66 to provide stops for limiting the relative vertical movement of the member 66 with respect to the member 64, and for generally providing bearing surfaces for rotation of the member 66. Spaces F formed between the rings 70, 71 and the sleeve 67 and the rings 68, 69 and the exterior surface of the member 66 allow a small portion of recirculated liquid to flow past, lubricating and centralizing the member 66 with respect to the member 64, and regulating its rise. Since the recirculated liquid is substantially clear, foul-up of the mechanism 63 is avoided.

Figure 7B:
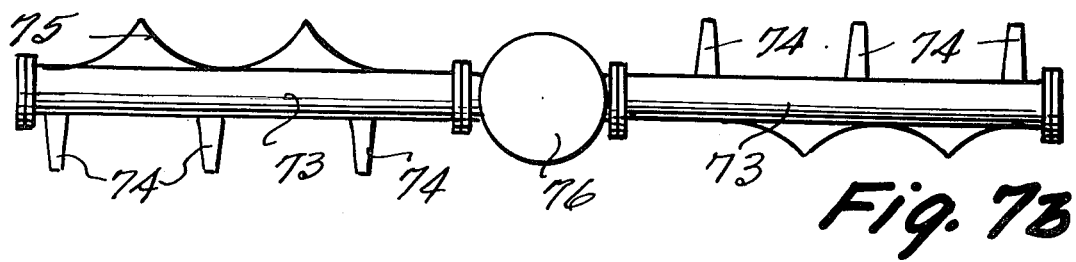
FIGS. 7a and 7b are cross-section and top views respectively of exemplary rotary mixing means that may be utilizable in the present invention.
Figure 7A:
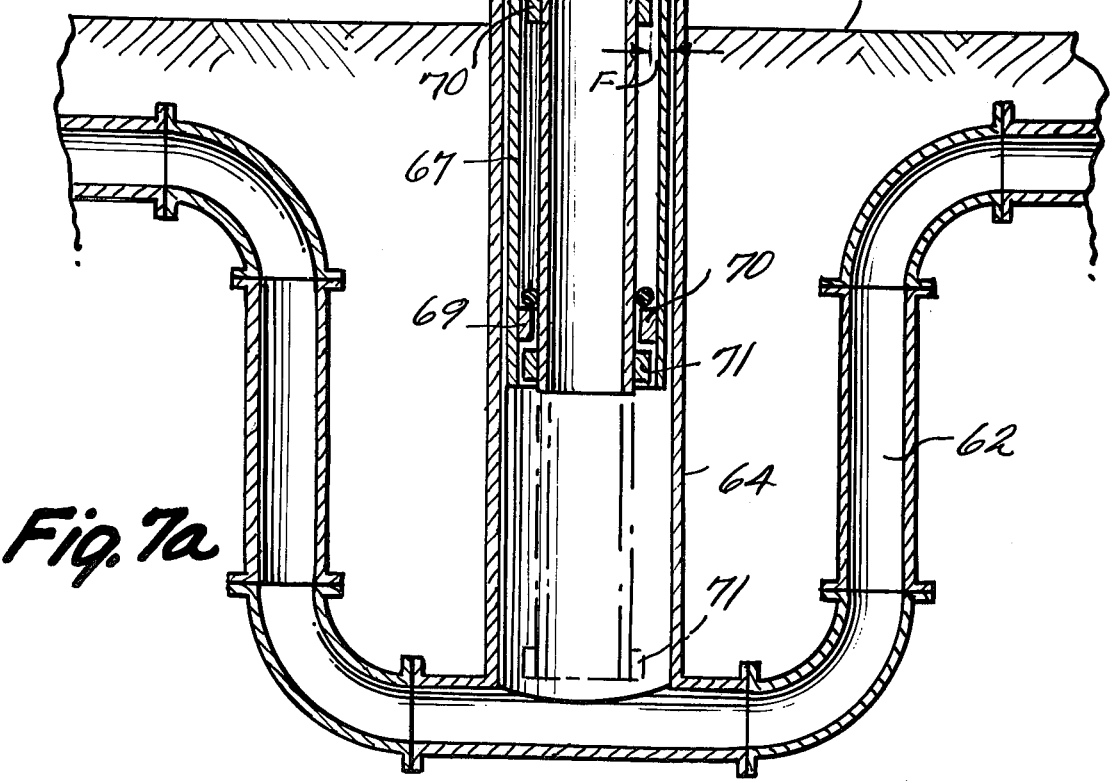

When the recirculating pump 58 is not operating, the rotor 63 assumes the general position shown in dotted line in FIG. 7a. When liquid under pressure is forced through the pipes 62, however, it pushes up on member 66, causing it to rise to generally the full line position shown in FIG. 7a, clearing any sediment which may resist rotation. The major portion of the liquid entering conduit 64 then flows up through conduit 66 to cause rotation of the means 63 and to be dispersed back into the mixing zone B, while some portion of the liquid will flow into zone B through spaces F.

A suitable mixing and rotative-force imparting structure 72 may be disposed on conduit 66. As shown in the drawings, the head 72 comprises a pair of arms 73 extending from either side of the central head member 76, and nozzle means 74 formed in side wall portions of said arms 73. The nozzle means 74 preferably comprises a plurality of nozzles formed in opposite side walls of the two arms 73 so that the jetting action of liquid under pressure passing through nozzles 74 will cause rotation of member 66 with respect to member 64. Vanes 75 or the like may be attached to means 72 (i.e. arms 73) to adjust the rate of vertical movement of the member 66 and/or to increase the mixing action caused by the rotation of the arms 73 in the zone B and the mixing caused by the introduction of fluid streams from nozzles 74 into the zone B.

It will thus be seen that sewage and other organic material containing liquid entering a digestor 14 through inlet 38 will pass through the mixing zone B, wherein it will be mixed by the mixers 63, through quiescent zone C, and over weir 50 and under skimmer 52 into clear zone D. After being retained under good thermal conditions in zones B, C, and D, the liquid at the top of zone D will be substantially clear and have most organic material removed therefrom by the anaerobic action of bacteria in the digestor 14, and may be removed through pipe 54 or the like to effluent system 18. Liquid from the bottom of zone D will be periodically or continuously recirculated to mixing zone B to facilitate mixing therein and to more fully remove organic material in the liquid in zone D.

Evolved Gas Collection and Removal

During anaerobic digestion of organic material in digestor(s) 14, significant amounts of methane gas and the like will be evolved. This is especially true when favorable temperature conditions within the digestor 14 are maintained (40°-65° C). This methane gas can be a valuable source of energy, and result in a significant net energy production from the operation of the facility 10. The primary components of the evolved gas collection system 16 comprise the flexible cover member 48 for digestor(s) 14, and means for withdrawing gas collected underneath the cover 48, shown generally at 80 in the drawings (see FIG. 4 especially).

The flexible cover 48 preferably consists of polyethylene, rubber, or other suitable flexible material that is not degradable by the action of evolved gases or the elements thereon. The material of cover 48 will not cause sparks when brought into rubbing contact with other portions of facility 10. The cover 48 is flexible so that it may assume any of the positions shown schematically in FIGS. 8a-8c, or any intermediate positions therebetween. The pressure of accumulated gas between the cover 48 and the surface of liquid in the digestor 14 will cause flexing of the cover 48 to assume its various positions.

The cover 48 is preferably an integral sheet of flexible material having peripheral edge portions 82 thereof, and center portions 83 thereof. Portions of cover 48 adjacent peripheral edge portions 82 are anchored so that the cover is not lifted away from the digestor 14 by evolved gases, and the edge portions 82 are disposed in liquid in digestor 14 below the liquid level E—E. In this way, a substantially gas-tight seal is provided between the interior of the cover 48 and the surface of the liquid in digestor 14 preventing entry of air to the digestor and escape of evolved gas therefrom. The cover 48 may preferably and advantageously be anchored by recirculating pipes 60 extending around the upper peripheral surface 46 of the digestor 14. As shown most clearly in FIG. 5b, the flexible cover may have the edge portions 82 thereof passed under the recirculating pipes 60 (between pipes 60 and surface 46), around a dowel 86 or the like disposed adjacent portions of pipes 60 spaced from the digestor 14, back under the pipe 60 and the portion of cover 48 already thereunder, and over the edge of the digestor 14, so that the edge portions 82 are disposed below the level E—E of liquid in digestor 14. The initial tension in the cover 48 may be adjusted when installing it, or suitable accessory tension adjusting means (not shown) may be provided. Accessory weight means or the like may be placed on pipes 60 or be associated with dowels 86 to provide for more secure anchoring of the cover 48 if desired.

Figure 8A:
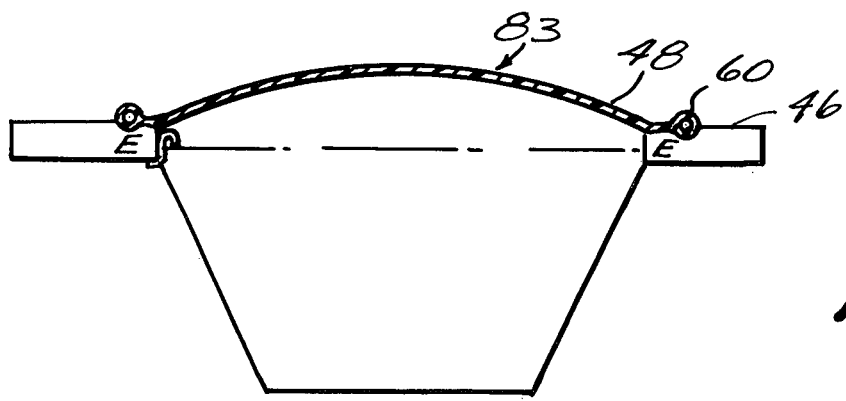
FIGS. 8a–8c are schematic side views of three positions that may be assumed by flexible cover means according to the present invention.
Figure 8B:
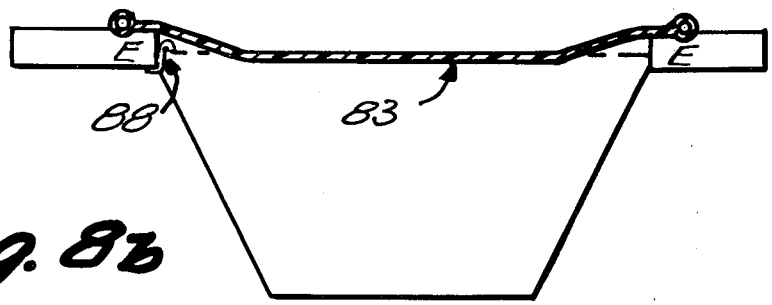
Figure 8C:
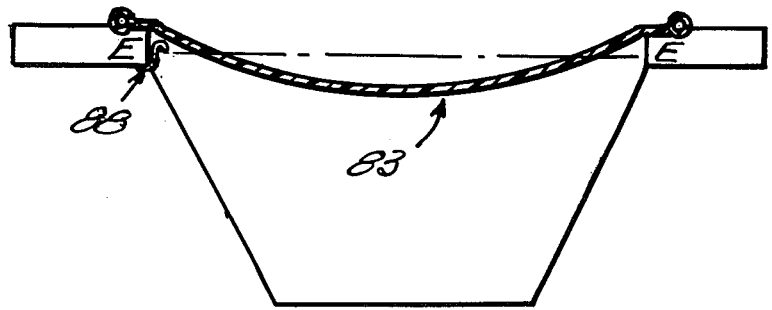

As gas collects under cover 48, means 80 are selectively operated for controlling the rate of removal of the gas from under the cover 48 to control which of the positions illustrated in FIGS. 8a-8c the cover 48 will assume. The means 80 preferably includes a gas removal structure, shown generally at 88 in FIG. 5b, a compressor 90 (FIG. 4), and pipe means 92 for interconnecting removal structure 88 with compressor 90, and for leading from compressor 90 to suitable gas storage, cleaning and/or utilization means (not shown). The removal structure 88 may comprise a pipe 94 having an open end 95 thereof above the liquid level E—E, and generally facing downwardly to receive gas in the open end 95 thereof. A floating ball 96 and associated guiding screen 97 or the like may be provided in association with end 95 for preventing the entry of water therein should the level E—E rise above a predetermined amount. The pipe 94 preferably passes through a wall 42 of the digestor 14 to the exterior thereof and compressor 90 so as not to interfere with the cover 48. Pipes 92 lead from pipe section 94 to compressor 90, wherein the collected gas is forced under pressure to suitable storage, cleaning, and/or utilization means. The operation of the compressor 90 is controllable to control the amount of gas that is withdrawn thereby from under the cover 48.

Figure 4:
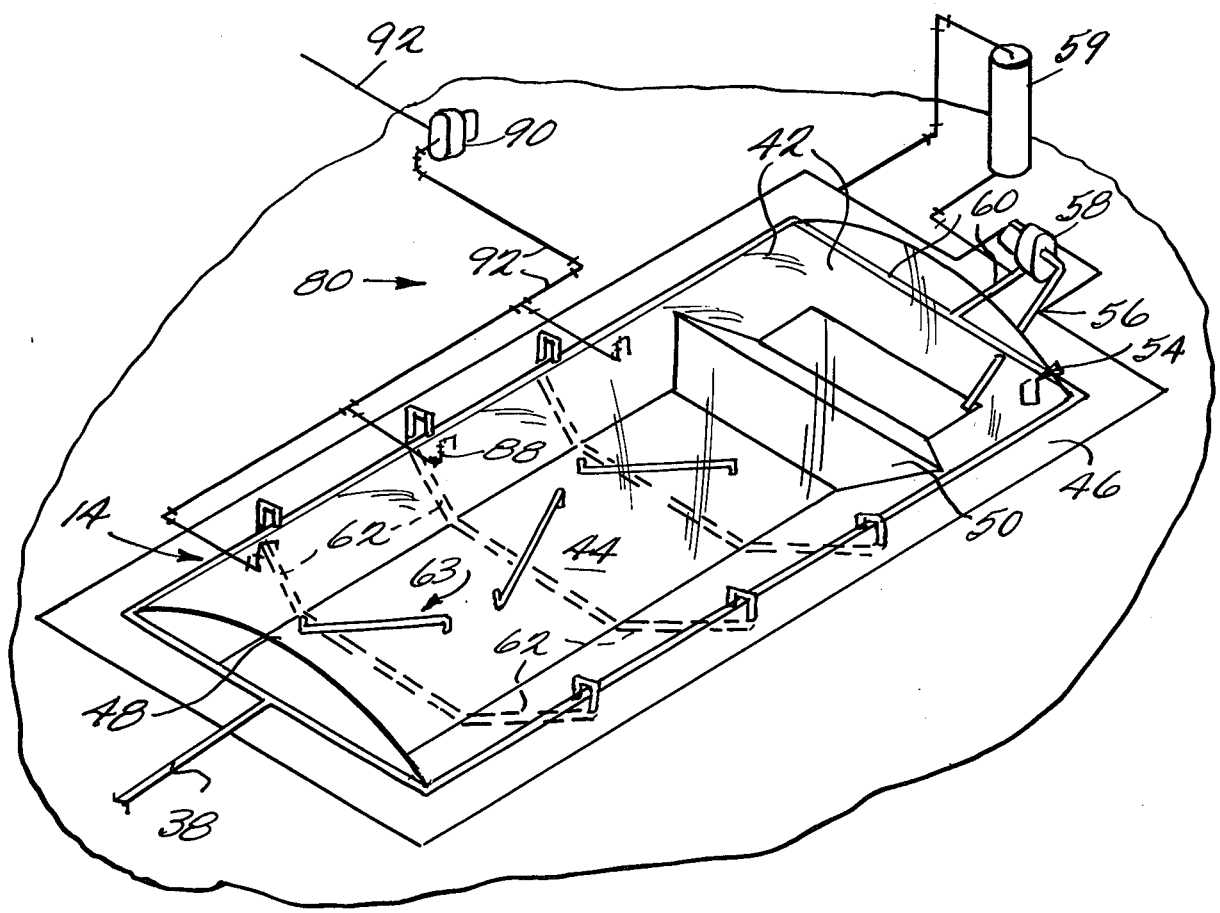
FIG. 4 is a diagrammatic perspective view of an exemplary digestor according to the present invention.

Although the cover 48 has been shown as transparent in FIG. 4 in order that the components of the digestor 14 might be easily seen, in practice, the cover 48 is usually of opaque radiant heat absorbing color and material. When the compressor 90 is controlled so that the cover 48 is inflated and assumes generally the position illustrated in FIG. 8a, the heat of the liquid in the digestor 14 is conserved by the gas space provided between the cover 48 and the liquid in digestor 14. This is the normal operating position of the facility 10. However, during initial start-up of the anaerobic digestion process, especially in cold weather, or under other circumstances, it may be desirable to provide extra heat to the liquid within digestor 14 rather than just conserving the heat therein. This may be accomplished by controlling the operation of compressor 90 so that the cover 48 assumes the position shown in FIG. 8b. In this position, the center portions 83 of the cover 48 are disposed on the surface of the liquid in digestor 14. The cover 48 may be made of material of density slightly less than that of water so that floating of middle portions 83 is facilitated. In this position, radiant heat absorbed by the cover 48 from the sun or the like is transferred directly to the liquid in the digestor 14, thereby facilitating heating thereof. Gas is removed from under the cover 48 where it collects around the periphery of the digestor 14 when the cover 48 is in the position shown in FIG. 8b (and 8c) since the means 88 are located adjacent the side walls 42 of the digestor 14.

For some reason should it be desirable to kill a batch of bacteria within the digestor 14, or if cooling was desired for some other reason, the compressor 90 can be controlled so that complete collapse of the cover 48 occurs, whereby the cover 48 assumes the general posture shown in FIG. 8c. In this position, the center portions 83 of the cover 48 are disposed below the liquid level E—E Liquid may also be disposed on the exterior of the cover 48 — as shown in FIG. 8c — in order to insure that the center portions 83 are below the liquid level E—E. It will thus be seen that means have been provided for the efficient collection of gases evolved from anaerobic digestion of organic material, which means may contribute to or conserve the heat of liquid having organic material being anaerobically digested.

As shown in FIG. 1, any number of digestors 14, gas collecting means 16, mixers 63, or like structures may be provided.

While the invention has been herein shown and described in what is presently conceived to be the most practical and preferred embodiment of the invention, it will be apparent to one of ordinary skill in the art that many modifications may be made thereof within the scope of the invention. For instance, suitable pressure relief means may be provided for the cover 48 and suitable overflow structures for the digestor liquid. Many other modifications are also possible, therefore it is intended that the invention be accorded the broadest scope of the appended claims in order to encompass all equivalent structures and devices.

What is claimed is:

1. An anaerobic waste treatment facility comprising
    a. a digestor having a bottom, side walls, an open top, said open top being defined by a peripheral top surface, and a cover for said open top said digestor adapted to hold a quantity of liquid containing organic matter to be digested therein, said liquid assuming a liquid level in said digestor, said digestor having an inlet, a mixing zone, a quiescent zone, a clear zone, and an outlet, said inlet providing entry of liquid into said mixing zone, and said outlet for removing liquid from said clear zone,
    b. means for preventing the entry of large particles from said quiescent zone into said clear zone, and
    c. means for selectively circulating liquid from said clear zone to said mixing zone and agitating the liquid in said mixing zone as liquid in introduced into said mixing zone from said clear zone, said means comprising a rotor member disposed below the liquid level of said digestor, and means formed in said rotor member for transferring the force of liquid circulating through said rotor into rotary movement of said rotor and rotary circulation of liquid from said rotor into liquid in said mixing zone, said rotor member comprising a first conduit member stationary with respect to said digestor, and a second conduit member movable generally vertically with respect to and rotatable with respect to said first member about a generally vertical axis of rotation, said second member moving vertically upwardly and rotating with respect to said first member upon the introduction of liquid under pressure into said first member, and means for limiting the vertical movement of said second member with respect to said first member so that said second member is always disposed below the level of liquid in said digestor.

2. A facility as recited in claim 1 wherein said means formed in said rotor member for transferring the force of liquid circulating through said rotor member comprises nozzle means formed in each of two generally horizontally extending conduit means extending from said second member and in liquid communication therewith.

3. A facility as recited in claim 2 wherein said first member has an interior sleeve and wherein said second member has an exterior surface facing said sleeve, said means for limiting the vertical movement of said second member with respect to said first member comprising a ring formed on said sleeve member adjacent the top thereof, and a ring formed on said exterior surface of said second member, said rings cooperating to provide a rotative bearing surface for rotation of said second member with respect to said first member.

4. A facility as recited in claim 3 wherein spaces are provided between said ring on said sleeve and a portion of the exterior surface of said second member adjacent said ring when said ring on said sleeve and said ring on said second member are in bearing engagement, and between said ring on said exterior surface of said second member and said sleeve, whereby a portion of the liquid flowing through said first conduit member will flow around said second conduit member through said spaces, lubricating the bearing surfaces provided by said rings.

* * * * *